United States Patent [19]

Lerman

[11] 4,338,937
[45] Jul. 13, 1982

[54] MECHANICAL CONTINENT ILEOSTOMY OR COLOSTOMY

[76] Inventor: Sheldon H. Lerman, 2202 Ken Oak Rd., Baltimore, Md. 21209

[21] Appl. No.: 213,337

[22] Filed: Dec. 5, 1980

[51] Int. Cl.³ .............................................. A61F 5/44
[52] U.S. Cl. .............................. 128/283; 128/DIG. 25
[58] Field of Search ................... 128/1, 283, DIG. 25

[56] References Cited

U.S. PATENT DOCUMENTS 3,952,726  4/1976  Hennig et al. ...................... 128/283
4,154,226  5/1979  Hennig et al. ...................... 128/283
4,217,664  8/1980  Faso ..................................... 128/283

Primary Examiner—C. Fred Rosenbaum
Attorney, Agent, or Firm—Fidelman, Wolffe & Waldron

[57] ABSTRACT

A mechanical continent ileostomy or colostomy device adapted for permanent insertion at the time of operation including a body portion having a flexible flange at one end, an insert portion attachable to the body portion and a stopper member having a central plug fitting into the insert. A plurality of permanent magnets embedded in a rim of the insert portion and in the stopper rim holds the stopper in sealing relationship to the insert.

3 Claims, 2 Drawing Figures

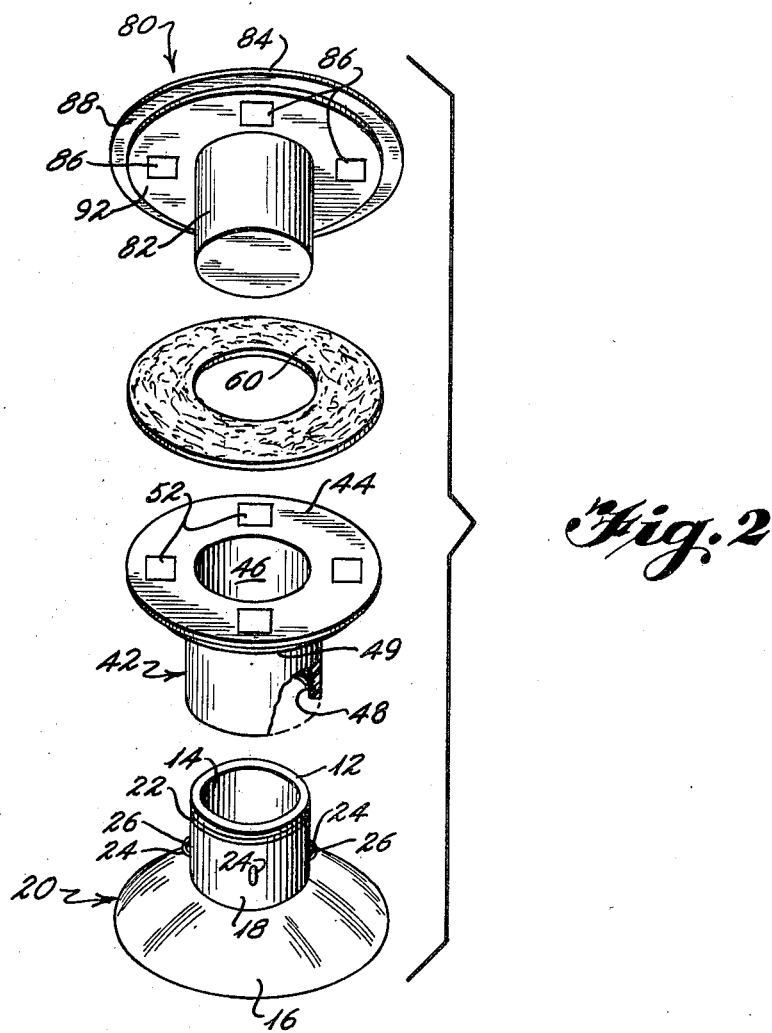
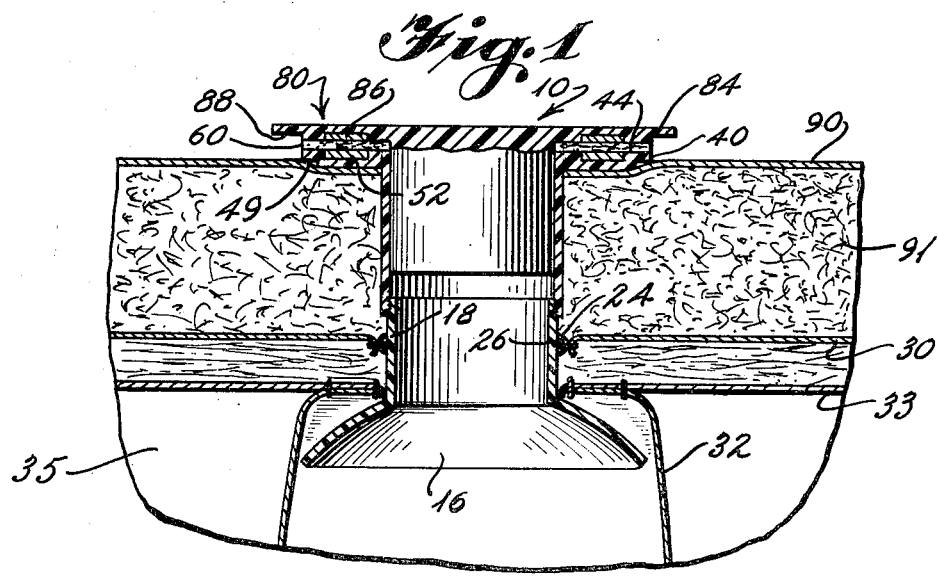

MECHANICAL CONTINENT ILEOSTOMY OR COLOSTOMY

BACKGROUND OF THE INVENTION

This invention relates to a mechanical continent ileostomy or colostomy adapted for long-term employment in human beings.

The object of this invention is to provide a continent cannula for the ileum or colon useful for evacuation of liquid and solid waste. The cannula may be inserted into the patient during the same operation as for the surgical construction of an ostomy, i.e., ileostomy or colostomy.

There is a need for a mechanical continent ileostomy and colostomy that is easy to insert at the time of operation. Insofar as is known to the inventor hereof, there currently is no mechanical continent ileostomy and only one mechanical continent colostomy utilized clinically. This mechanical continent colostomy is described in an article by H. Feustal and G. Henning entitled, "Kintinente Kolostomie durch Magnetverschluss" which appeared in *Dtsch. Med. Wochenschr.*, Vol. 100: p. 1063 (1975), and further discussed by Golligher, et al., *Brit. J. Surg.* 64 (1977), pp. 501–507.

However, animal test studies have long employed what is known in the art as the Thomas cannula to form a continent ostomy in instances wherein controlled access to the intestinal tract is required by the experiment. This device is described in an article by J. E. Thomas, J. O. Crider and C. J. Mogan entitled, "A Study of Reflexes Involving the Pyloric Sphincter and Antrum and Their Role in Gastric Evacuation", published in *Am. J. Physiol.*, Vol. 108, pp. 683–700 (1934). The Thomas cannula is not believed to be well adapted for human ostomy purposes.

SUMMARY OF THE INVENTION

Briefly stated, the present ostomy device comprises three elements as in the Thomas cannula, namely a hollow body member adapted to be introduced into the bowel, a hollow insert member fitted to the body and a stopper member. In the ostomy device of this invention, both the insert and the body members contact body tissues and are intended for permanent placement, while the stopper is readily removable so as to allow discharge through the ostomy device.

Although it is principally adapted for human ostomy usage, the cannula of this invention may be employed for animal test studies in substitution for the Thomas cannula.

BRIEF DESCRIPTION OF THE DRAWING

FIG. 1 is a diagrammatic cross-sectional view of the cannula in place;

FIG. 2 is an exploded, oblique view of the cannula parts.

DISCUSSION OF THE INVENTION

As is illustrated in the Figures, the cannula 10 of this invention provides for a mechanical continent ileostomy or colostomy. The cannula is comprised of the following parts: a body member 20, an insert member 40, an annular washer or gasket 60 and a stopper member 80.

As is best illustrated in FIG. 2, body member 20 comprises a hollow cylindrical stem 12 having passageway 14 therethrough that terminates in a flange bottom 16 which desirably is convex in shape. At the upper end of the cylindrical stem 12 are screw threads 22 on the exterior surface. Also on the exterior surface 18 of stem 12 are a multiplicity of tangs 24 to provide suture holes 26 on body 20, four tangs 24 spaced apart around the periphery of stem 12, being a suitable number. Placement of a set of non-absorbable sutures through holes 26 and through fascia 30 fix body 20 to fascia 30 hold body 20 in place relative to fascia 30 and secure body 20 against rotation when insert 40 is screwed on to the external threads 22 on the stem 12.

Body 20 is formed from a medically acceptable plastic material, e.g., polyethylene, polymethylmethacrylate, Teflon ®. Although the stem 12 of body 20 may be relatively rigid, flange 16 is relatively thin and pliable so it can cap intestine 32 by conversion to a more convex shape. The edge of flange 16 is soft and rounded-off to prevent puncture of intestine 32 upon body movement. Following insertion of the flange 16 through the incised end of the intestine 32, a purse string suture previously placed in the intestinal serosa is tightened to bring the severed edge of intestine 32 up around flange 16 in contact with the outer wall surface of stem 12. In addition, the intestine 32 is sutured to the parietal peritoneum 33 of the abdominal wall. Then the tangs 24 on body 20 are sutured to fascia 30. This sets body 20 in permanent position ready to be secured to insert member 40.

As shown in FIG. 2, the insert 40 is comprised of a stem portion 42 and rim portion 44. Stem portion 42, which is cylindrical, is sized to fit on the stem 12 of body 20. On the interior surface 46 of insert 40 at the lower end of stem 42 are screw threads 48 which match threads 22 on body 20 so that insert 40 may be screwed to body 20. In passing, it may be noted that the thread location may be reversed, i.e., be inside of body 20 and outside of insert 40.

Rim 44 contains a set of magnets 52 sealed within the material from which the insert 40 is made. Insert 40, too, is formed from a medically acceptable plastic material. The insert 40 should be available to the surgeon in different lengths to adjust to the varying thickness of human abdominal wall, patient to patient. Desirably, the rim portion 44 of insert 40 will nearly seat on the patient's skin 90, and to that end an appropriate length cap will be selected. Rim 44 may be provided with a small overhang or lip 49 for convenient attachment thereto of a flexible conduit (not shown) for convenience in fecal evacuation. Such a flexible conduit may be elastically fitted over the lip 48 of rim 44 and wastes removed by compressing the conduit sending the fecal material out through the open end into an appropriate receptacle.

The stopper 80 is comprised of a plug portion 82 and a cap portion 84. Inside the plastic material of cap 84 is a set of magnets 86. Plug 82 is of a diameter appropriate to fit into the cylindrical space inside the stem 42 of insert 40 as is illustrated in FIG. 1. The length of the plug is not important (other than that it should not extend into body 20). The plug 82, stem 40 and stem 12 are all co-axial.

Desirably stopper cap 84 is constructed to that there is a small overhang 88 at the rim, which overhang enables the user to overcome the magnetic force generated by magnets 86 and 52 and lift stopper 80 from insert 40.

A disposable annular washer or gasket 60 is affixed to the bottom surface 92 of stopper cap 84 to assure a watertight seal between stopper 80 and insert 40. Washer 60 may be a sleeve that covers plug 82.

The cannula of this invention is inserted as follows:

To accommodate placement of the device in the abdominal wall, an auxiliary skin incision is made on the abdomen and extended into the peritoneal cavity 35. From this incision, the stem 12 of body 20 is grasped by a hemostat and pulled into the incision enough to bow the peritoneal cavity outward. At this stage in the overall surgical procedure, the intestine 32 has already been securely fastened around flange 16 of body 20 and to the parietal peritoneum 33. Once the stem 12 is elevated partially out of the peritoneal cavity into the auxilliary skin incision, the fascia 30 is sutured to itself and to the suture holder tangs 24. Doing so prevents axial rotation of body 20 and prevents body 20 from inadvertently exiting from the abdomen.

A proper length size insert 40 is then attached to body 20, threading same by inner screw threads 48 thereon to the outer screw threads 22 on body 20. Once insert and body are secured together, the subcutaneous tissue 91 and skin 90 are closed around insert 40. Stopper cap 80 is added some time subsequently.

The cannula of this invention is made in different diameters for use with different sections of the intestine and different lengths of insert 40 are provided. However, the technique of insertion remains the same for all sizes, i.e., sterile techniques under general anesthesia.

The cannula of this invention becomes a permanent attachment to the human intestine allowing control of egress of human intestinal waste therethrough.

It may be seen from the foregoing description that this invention provides a cannulation approach adapted for providing controlled egress of fecal matter from the intestines. The cannula does not cause interference with blood circulation and a resulting necrosis of compressed abdominal wall tissues. The tissues are held gently, even though firmly, between the cap 44 and the flange 16.

The continent cannula of this invention may be situated in the abdominal wall and in the ileum or colon for an indefinite period of time without causing necrosis, infection, or degeneration of the tissues thereof due to contact with this foreign body. Moreover, the use of the continent cannula affords minimal risk of contamination of the peritoneal cavity and of the abdominal wall and skin surface by intestinal contents.

Since the cannula is anchored by non-absorbable sutures to the readily accessible Scarpe's fascia in the abdominal wall, the cannula can be easily removed by a minor surgical procedure, if such becomes required and the stoma extended through the incision.

Thus, as is apparent from the foregoing, the cannula of this invention provides a continent outlet for the evacuation of intestinal waste through the stems 12 and 42. The magnetic cap 80 removably seals the stems through magnetic forces until the person wishes to remove the cap.

Placement of the lower set of magnets 52 outside of skin 90, as is done with the cannula of this invention, allows the magnetic forces to remain the same person to person, i.e., neither too small nor large since the magnets 52, 86 are always spaced apart the thickness of the material in which they are embedded and the depth of washer 60. The magnets themselves may be of any permanent strongly magnetic material.

If desired, the washer 60 may be constructed of a charcoal containing gas permeable, liquid impermeable material so as to allow gradual largely non-odorous escape of flatus from the intestine without need to unstick the cap.

I claim:

1. A mechanical continent ostomy device comprising:
    a body portion in the shape of a cylindrical stem surmounting a flexible flange with screw threads present on the stem at the end thereof opposing said flange;
    an insert portion in the shape of a cylindrical stem with a rim at one end thereof, the rim having at least one permanent magnet therein, the insert stem having screw threads present thereon at the end thereof opposing said rim;
    the screw threads on said body and the screw threads on said insert being matched whereby a male-female coupling of insert and body may be made;
    a stopper member in the shape of a rimmed plug, the plug portion being sized to fit into said insert, and the rim portion being sized to fit superposed on the insert rim, said stopper having at least one permanent magnet being present inside the rim thereof, whereby said stopper and said insert may be magnetically coupled rim to rim; and
    a disposable washer member, adapted to fit between the rims.

2. The ostomy device of claim 1 including internal threads on the insert stem and external threads on the body stem.

3. The ostomy device of claim 1 wherein tangs are present on the outside of the body stem, for use in suturing the body in place.

* * * * *